(12) United States Patent
Ryan

(10) Patent No.: US 7,270,660 B2
(45) Date of Patent: *Sep. 18, 2007

(54) APPARATUS AND METHOD FOR SEALING AND CUTTING TISSUE

(75) Inventor: Thomas Patrick Ryan, Fort Collins, CO (US)

(73) Assignee: Sherwood Services AG, Schaffhausen (CH)

( * ) Notice: Subject to any disclaimer, the term of this patent is extended or adjusted under 35 U.S.C. 154(b) by 75 days.

This patent is subject to a terminal disclaimer.

(21) Appl. No.: 11/170,616

(22) Filed: Jun. 29, 2005

(65) Prior Publication Data

US 2006/0020265 A1    Jan. 26, 2006

Related U.S. Application Data

(63) Continuation of application No. 09/992,301, filed on Nov. 14, 2001, now Pat. No. 6,932,810, which is a continuation of application No. 09/591,328, filed on Jun. 9, 2000, now abandoned, which is a continuation of application No. 08/925,805, filed on Sep. 9, 1997, now Pat. No. 6,267,761.

(51) Int. Cl.
  *A61B 18/14*    (2006.01)
(52) U.S. Cl. ........................... 606/38; 606/51; 600/547
(58) Field of Classification Search ...................... None
  See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 2,002,594 A | 5/1935 | Wappler et al. |

(Continued)

FOREIGN PATENT DOCUMENTS

CA    2104423    2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner*—Glenn K. Dawson

(57) ABSTRACT

An axial elongate bipolar tissue sealer/cutter and method of use by a surgeon for electrosurgery on tissue. A chassis on a handle extends axially for axial movement. An effector on a distal end of the chassis first contacts tissue with axial movement. The effector provides bipolar electrosurgery. A member extending from the distal end is opposite the patient end of a tube. A part on the member is transverse to the axis to conduct electrosurgery. First and second bipolar electrodes on the effector and part are electrically isolated. A generator for bipolar electrosurgery supplies the electrodes. An activator is movably supported on the handle connects to the tube and/or chassis to axially move the patient end and its effector relative to the part. Tissue and bodily fluid therebetween are sealed or cut through application of compression and bipolar electrosurgery between the first and second electrodes. The effector and the part have complimentary sealing or cutting surfaces for partial mating engagement upon axial movement toward one another.

8 Claims, 6 Drawing Sheets

U.S. PATENT DOCUMENTS

| | | |
|---|---|---|
| 2,011,169 A | 8/1935 | Wappler |
| 2,031,682 A | 2/1936 | Wappler et al. |
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |
| 4,041,952 A | 8/1977 | Morrison, Jr. et al. |
| 4,074,718 A | 2/1978 | Morrison, Jr. |
| 4,088,134 A | 5/1978 | Mazzariello |
| 4,128,099 A | 12/1978 | Bauer |
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A * | 3/1993 | Parins ................. 606/48 |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A * | 4/1995 | Yates et al. .................. 606/50 |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,671 A * | 9/1996 | Yates ................. 606/38 |
| 5,558,672 A | 9/1996 | Edwards et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,535 A | 11/1996 | Viklund |
| 5,582,611 A | 12/1996 | Tsukagoshi et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |
| 5,611,798 A | 3/1997 | Eggers |
| 5,626,578 A | 5/1997 | Tihon |
| 5,626,609 A | 5/1997 | Zvenyatsky et al. |

| | | | | | |
|---|---|---|---|---|---|
| 5,630,833 A | 5/1997 | Katsaros et al. | 6,004,335 A | 12/1999 | Vaitekunas et al. |
| 5,637,110 A | 6/1997 | Pennybacker et al. | 6,010,516 A | 1/2000 | Hulka et al. |
| 5,643,294 A | 7/1997 | Tovey et al. | 6,024,741 A | 2/2000 | Williamson et al. |
| 5,647,869 A | 7/1997 | Goble et al. | 6,024,744 A | 2/2000 | Kese et al. |
| 5,647,871 A | 7/1997 | Levine et al. | 6,033,399 A | 3/2000 | Gines |
| 5,649,959 A | 7/1997 | Hannam et al. | 6,039,733 A | 3/2000 | Buysse et al. |
| 5,658,281 A | 8/1997 | Heard | 6,041,679 A | 3/2000 | Slater et al. |
| 5,662,667 A | 9/1997 | Knodel | 6,050,996 A | 4/2000 | Schmaltz et al. |
| 5,665,100 A | 9/1997 | Yoon | 6,053,914 A | 4/2000 | Eggers et al. |
| 5,667,526 A | 9/1997 | Levin | 6,053,933 A | 4/2000 | Balazs et al. |
| 5,674,220 A | 10/1997 | Fox et al. | D424,694 S | 5/2000 | Tetzlaff et al. |
| 5,681,282 A | 10/1997 | Eggers et al. | D425,201 S | 5/2000 | Tetzlaff et al. |
| 5,693,051 A | 12/1997 | Schulze et al. | 6,059,782 A | 5/2000 | Novak et al. |
| 5,695,522 A | 12/1997 | LeMaire, III et al. | RE36,795 E | 7/2000 | Rydell |
| 5,700,261 A | 12/1997 | Brinkerhoff | 6,083,223 A | 7/2000 | Baker |
| 5,702,390 A | 12/1997 | Austin et al. | 6,086,586 A | 7/2000 | Hooven |
| 5,707,369 A | 1/1998 | Vaitekunas et al. | 6,090,107 A | 7/2000 | Borgmeier et al. |
| 5,709,680 A | 1/1998 | Yates et al. | 6,096,037 A | 8/2000 | Mulier et al. |
| 5,716,366 A | 2/1998 | Yates | 6,099,550 A | 8/2000 | Yoon |
| 5,720,744 A | 2/1998 | Eggleston et al. | 6,102,909 A | 8/2000 | Chen et al. |
| 5,727,428 A | 3/1998 | LeMaire, III et al. | 6,110,171 A | 8/2000 | Rydell |
| 5,735,848 A | 4/1998 | Yates et al. | 6,113,596 A | 9/2000 | Hooven et al. |
| 5,743,906 A | 4/1998 | Parins et al. | 6,113,598 A | 9/2000 | Baker |
| 5,755,717 A | 5/1998 | Yates et al. | 6,123,701 A | 9/2000 | Nezhat |
| 5,766,130 A | 6/1998 | Selmonosky | H1904 H | 10/2000 | Yates et al. |
| 5,766,166 A | 6/1998 | Hooven | 6,126,658 A | 10/2000 | Baker |
| 5,766,170 A | 6/1998 | Eggers | 6,152,923 A | 11/2000 | Ryan |
| 5,769,849 A | 6/1998 | Eggers | 6,174,309 B1 | 1/2001 | Wrublewski et al. |
| 5,772,655 A | 6/1998 | Bauer et al. | 6,179,834 B1 | 1/2001 | Buysse et al. |
| 5,772,670 A | 6/1998 | Brosa | 6,179,837 B1 | 1/2001 | Hooven |
| 5,776,128 A | 7/1998 | Eggers | 6,183,467 B1 | 2/2001 | Shapeton et al. |
| 5,776,130 A | 7/1998 | Buysse et al. | 6,187,003 B1 | 2/2001 | Buysse et al. |
| 5,779,701 A | 7/1998 | McBrayer et al. | 6,190,386 B1 | 2/2001 | Rydell |
| 5,792,137 A | 8/1998 | Carr et al. | 6,193,718 B1 | 2/2001 | Kortenbach et al. |
| 5,792,177 A | 8/1998 | Kaseda | 6,206,877 B1 | 3/2001 | Kese et al. |
| 5,797,938 A | 8/1998 | Paraschac et al. | 6,217,602 B1 | 4/2001 | Redmon |
| 5,797,958 A | 8/1998 | Yoon | 6,224,593 B1 | 5/2001 | Ryan et al. |
| 5,800,449 A | 9/1998 | Wales | 6,228,080 B1 | 5/2001 | Gines |
| 5,807,393 A | 9/1998 | Williamsom, IV et al. | 6,228,083 B1 | 5/2001 | Lands et al. |
| 5,810,808 A | 9/1998 | Eggers | 6,267,761 B1 * | 7/2001 | Ryan .......................... 606/50 |
| 5,810,811 A | 9/1998 | Yates et al. | 6,270,508 B1 | 8/2001 | Klieman et al. |
| 5,814,043 A | 9/1998 | Shapeton | 6,273,887 B1 | 8/2001 | Yamauchi et al. |
| 5,817,093 A | 10/1998 | Williamson, IV et al. | 6,277,117 B1 | 8/2001 | Tetzlaff et al. |
| 5,820,630 A | 10/1998 | Lind | 6,280,458 B1 | 8/2001 | Boche et al. |
| 5,827,271 A | 10/1998 | Buysse et al. | 6,283,961 B1 | 9/2001 | Underwood et al. |
| 5,827,279 A | 10/1998 | Hughett et al. | D449,886 S | 10/2001 | Tetzlaff et al. |
| 5,827,281 A | 10/1998 | Levin | 6,322,561 B1 | 11/2001 | Eggers et al. |
| 5,833,690 A | 11/1998 | Yates et al. | 6,334,860 B1 | 1/2002 | Dorn |
| 5,843,080 A | 12/1998 | Fleenor et al. | 6,334,861 B1 | 1/2002 | Chandler et al. |
| 5,849,022 A | 12/1998 | Sakashita et al. | 6,350,264 B1 | 2/2002 | Hooven |
| 5,853,412 A | 12/1998 | Mayenberger | 6,352,536 B1 | 3/2002 | Buysse et al. |
| 5,860,976 A | 1/1999 | Billings et al. | D457,958 S | 5/2002 | Dycus et al. |
| 5,876,401 A | 3/1999 | Schulze et al. | D457,959 S | 5/2002 | Tetzlaff et al. |
| 5,891,141 A | 4/1999 | Rydell | 6,387,094 B1 | 5/2002 | Eitenmuller |
| 5,891,142 A | 4/1999 | Eggers et al. | 6,398,779 B1 | 6/2002 | Buysse et al. |
| 5,893,863 A | 4/1999 | Yoon | 6,402,747 B1 | 6/2002 | Lindemann et al. |
| 5,893,875 A | 4/1999 | O'Connor et al. | 6,409,728 B1 | 6/2002 | Ehr et al. |
| 5,902,301 A | 5/1999 | Olig | H2037 H | 7/2002 | Yates et al. |
| 5,906,630 A | 5/1999 | Anderhub et al. | 6,419,675 B1 | 7/2002 | Gallo, Sr. |
| 5,908,420 A | 6/1999 | Parins et al. | 6,425,896 B1 | 7/2002 | Baltschun et al. |
| 5,911,719 A | 6/1999 | Eggers | 6,440,144 B1 | 8/2002 | Bacher |
| 5,913,874 A | 6/1999 | Berns et al. | 6,443,952 B1 | 9/2002 | Mulier et al. |
| 5,921,984 A | 7/1999 | Sutcu et al. | 6,443,970 B1 | 9/2002 | Schulze et al. |
| 5,925,043 A | 7/1999 | Kumar et al. | 6,451,018 B1 | 9/2002 | Lands et al. |
| 5,935,126 A | 8/1999 | Riza | 6,458,128 B1 | 10/2002 | Schulze |
| 5,944,718 A | 8/1999 | Dafforn et al. | 6,458,130 B1 | 10/2002 | Frazier et al. |
| 5,951,549 A | 9/1999 | Richardson et al. | 6,464,701 B1 | 10/2002 | Hooven et al. |
| 5,954,720 A | 9/1999 | Wilson et al. | 6,464,702 B2 | 10/2002 | Schulze et al. |
| 5,957,923 A | 9/1999 | Hahnen et al. | 6,464,704 B2 | 10/2002 | Schmaltz et al. |
| 5,961,514 A | 10/1999 | Long et al. | 6,511,480 B1 | 1/2003 | Tetzlaff et al. |
| 5,976,132 A | 11/1999 | Morris | 6,585,735 B1 | 7/2003 | Frazier et al. |
| 5,984,939 A | 11/1999 | Yoon | 6,602,252 B2 | 8/2003 | Mollenauer |
| 5,989,277 A | 11/1999 | LeMaire, III et al. | 6,620,161 B2 | 9/2003 | Schulze et al. |

| | | | | | | |
|---|---|---|---|---|---|---|
| 6,626,901 B1 | 9/2003 | Treat et al. | | 2004/0249371 A1 | 12/2004 | Dycus et al. |
| 6,652,521 B2 | 11/2003 | Schulze | | 2004/0249374 A1 | 12/2004 | Tetzlaff et al. |
| 6,656,177 B2 | 12/2003 | Truckai et al. | | 2004/0250419 A1 | 12/2004 | Sremcich et al. |
| 6,660,072 B2 | 12/2003 | Chatterjee | | 2004/0254573 A1 | 12/2004 | Dycus et al. |
| 6,669,696 B2 | 12/2003 | Bacher et al. | | 2005/0004564 A1 | 1/2005 | Wham et al. |
| 6,682,527 B2 | 1/2004 | Strul | | 2005/0004568 A1 | 1/2005 | Lawes et al. |
| 6,682,528 B2 | 1/2004 | Frazier et al. | | 2005/0004570 A1 | 1/2005 | Chapman et al. |
| 6,695,840 B2 | 2/2004 | Schulze | | 2005/0021025 A1 | 1/2005 | Buysse et al. |
| 6,726,686 B2 | 4/2004 | Buysse et al. | | 2005/0021026 A1 | 1/2005 | Baily |
| 6,733,498 B2 | 5/2004 | Paton et al. | | 2005/0021027 A1 | 1/2005 | Shields et al. |
| 6,743,229 B2 | 6/2004 | Buysse et al. | | 2005/0033278 A1 | 2/2005 | McClurken et al. |
| 6,770,072 B1 | 8/2004 | Truckai et al. | | 2005/0101951 A1 | 5/2005 | Wham et al. |
| 6,773,434 B2 | 8/2004 | Ciarrocca | | 2005/0101952 A1 | 5/2005 | Lands et al. |
| 6,776,780 B2 | 8/2004 | Mulier et al. | | 2005/0107784 A1 | 5/2005 | Moses et al. |
| D496,997 S | 10/2004 | Dycus et al. | | 2005/0107785 A1 | 5/2005 | Dycus et al. |
| 6,802,843 B2 | 10/2004 | Truckai et al. | | 2005/0113818 A1 | 5/2005 | Sartor et al. |
| D499,181 S | 11/2004 | Dycus et al. | | 2005/0113819 A1 | 5/2005 | Wham et al. |
| 6,818,000 B2 | 11/2004 | Muller et al. | | 2005/0113826 A1 | 5/2005 | Johnson et al. |
| 6,860,880 B2 | 3/2005 | Treat et al. | | 2005/0113827 A1 | 5/2005 | Dumbauld et al. |
| 6,926,716 B2 | 8/2005 | Baker et al. | | 2005/0113828 A1 | 5/2005 | Shields et al. |
| 6,929,644 B2 | 8/2005 | Truckai et al. | | 2005/0119655 A1 | 6/2005 | Moses et al. |
| 6,932,810 B2 * | 8/2005 | Ryan .......................... 606/38 | | 2005/0149151 A1 | 7/2005 | Orszulak et al. |
| 6,942,662 B2 | 9/2005 | Goble et al. | | 2006/0064085 A1 | 3/2006 | Schechter et al. |
| 6,964,662 B2 | 11/2005 | Kidooka | | 2006/0079891 A1 | 4/2006 | Arts et al. |
| 7,033,354 B2 | 4/2006 | Keppel | | 2006/0129146 A1 | 6/2006 | Dycus et al. |
| 7,083,618 B2 | 8/2006 | Couture et al. | | 2006/0161150 A1 | 7/2006 | Keppel |
| 7,090,673 B2 | 8/2006 | Dycus et al. | | 2006/0167450 A1 | 7/2006 | Johnson et al. |
| 7,101,371 B2 | 9/2006 | Dycus et al. | | 2006/0167452 A1 | 7/2006 | Moses et al. |
| 7,101,372 B2 | 9/2006 | Dycus et al. | | 2006/0173452 A1 | 8/2006 | Buysse et al. |
| 7,101,373 B2 | 9/2006 | Dycus et al. | | 2006/0189980 A1 | 8/2006 | Johnson et al. |
| 7,103,947 B2 | 9/2006 | Sartor et al. | | 2006/0189981 A1 | 8/2006 | Dycus et al. |
| 7,118,570 B2 | 10/2006 | Tetzlaff et al. | | 2006/0190035 A1 | 8/2006 | Hushka et al. |
| 7,118,587 B2 | 10/2006 | Dycus et al. | | 2006/0217709 A1 | 9/2006 | Couture et al. |
| 2002/0013583 A1 | 1/2002 | Camran et al. | | 2006/0224158 A1 | 10/2006 | Odom et al. |
| 2002/0099372 A1 | 7/2002 | Schulze et al. | | | | |
| 2002/0107517 A1 | 8/2002 | Witt et al. | | | FOREIGN PATENT DOCUMENTS | |
| 2002/0111624 A1 | 8/2002 | Witt et al. | | | | |
| 2002/0188294 A1 | 12/2002 | Couture et al. | | DE | 2415263 | 10/1975 |
| 2003/0014052 A1 | 1/2003 | Buysse et al. | | DE | 87 12328 | 3/1988 |
| 2003/0014053 A1 | 1/2003 | Nguyen et al. | | DE | 19608716 | 4/1997 |
| 2003/0018331 A1 | 1/2003 | Dycus et al. | | DE | 19751108 | 5/1999 |
| 2003/0018332 A1 | 1/2003 | Schmaltz et al. | | EP | 0364216 A1 | 4/1990 |
| 2003/0032956 A1 | 2/2003 | Lands et al. | | EP | 0518230 A1 | 12/1992 |
| 2003/0069571 A1 | 4/2003 | Treat et al. | | EP | 541 930 B1 | 5/1993 |
| 2003/0078578 A1 | 4/2003 | Truckai et al. | | EP | 0572131 | 12/1993 |
| 2003/0109875 A1 | 6/2003 | Tetzlaff et al. | | EP | 584787 A1 | 3/1994 |
| 2003/0139741 A1 | 7/2003 | Goble et al. | | EP | 0623316 A1 | 11/1994 |
| 2003/0139742 A1 | 7/2003 | Wampler et al. | | EP | 0624348 A2 | 11/1994 |
| 2003/0158549 A1 | 8/2003 | Swanson | | EP | 0650701 A1 | 5/1995 |
| 2003/0181910 A1 | 9/2003 | Dycus et al. | | EP | 0694290 A3 | 3/1996 |
| 2003/0199869 A1 | 10/2003 | Johnson et al. | | EP | 0717966 A1 | 6/1996 |
| 2003/0216732 A1 | 11/2003 | Truckai et al. | | EP | 0754437 A3 | 3/1997 |
| 2003/0220637 A1 | 11/2003 | Truckai et al. | | EP | 853922 A1 | 7/1998 |
| 2003/0229344 A1 | 12/2003 | Dycus et al. | | EP | 0875209 A1 | 11/1998 |
| 2003/0236325 A1 | 12/2003 | Bonora | | EP | 0878169 A1 | 11/1998 |
| 2004/0030330 A1 | 2/2004 | Brassell et al. | | EP | 0887046 A3 | 1/1999 |
| 2004/0030332 A1 | 2/2004 | Knowlton et al. | | EP | 0923907 A1 | 6/1999 |
| 2004/0049185 A1 | 3/2004 | Latterell et al. | | EP | 0986990 A1 | 3/2000 |
| 2004/0082952 A1 | 4/2004 | Dycus et al. | | EP | 1034747 A1 | 9/2000 |
| 2004/0087943 A1 | 5/2004 | Dycus et al. | | EP | 1034748 A1 | 9/2000 |
| 2004/0115296 A1 | 6/2004 | Duffin | | EP | 1025807 A3 | 10/2000 |
| 2004/0116924 A1 | 6/2004 | Dycus et al. | | EP | 1034746 A3 | 10/2000 |
| 2004/0116979 A1 | 6/2004 | Truckai et al. | | EP | 1050278 A1 | 11/2000 |
| 2004/0122423 A1 | 6/2004 | Dycus et al. | | EP | 1053719 A1 | 11/2000 |
| 2004/0143263 A1 | 7/2004 | Schechter et al. | | EP | 1053720 A1 | 11/2000 |
| 2004/0147925 A1 | 7/2004 | Buysse et al. | | EP | 1055399 A1 | 11/2000 |
| 2004/0162557 A1 | 8/2004 | Tetzlaff et al. | | EP | 1055400 A1 | 11/2000 |
| 2004/0176762 A1 | 9/2004 | Lawes et al. | | EP | 1080694 A1 | 3/2001 |
| 2004/0193153 A1 | 9/2004 | Sarter et al. | | EP | 1082944 A1 | 3/2001 |
| 2004/0225288 A1 | 11/2004 | Buysse et al. | | EP | 1159926 A2 | 12/2001 |
| 2004/0230189 A1 | 11/2004 | Keppel | | EP | 1330991 A1 | 7/2003 |
| 2004/0236325 A1 | 11/2004 | Tetzlaff et al. | | EP | 1486177 A2 | 6/2004 |
| 2004/0243125 A1 | 12/2004 | Dycus et al. | | EP | 1532932 A1 | 5/2005 |

| | | | |
|---|---|---|---|
| GB | 2214430 A | 6/1989 | |
| JP | 501068 | 9/1984 | |
| JP | 502328 | 3/1992 | |
| JP | 5-40112 | 2/1993 | |
| JP | 06343644 A2 | 12/1994 | |
| JP | 07265328 A2 | 10/1995 | |
| JP | 08056955 A2 | 3/1996 | |
| JP | 08252263 A2 | 10/1996 | |
| JP | 09010223 A2 | 1/1997 | |
| JP | 11244298 A2 | 9/1999 | |
| JP | 2000342599 A2 | 12/2000 | |
| JP | 2000350732 A2 | 12/2000 | |
| JP | 2001008944 A2 | 1/2001 | |
| JP | 2001029356 A2 | 2/2001 | |
| JP | 2001128990 A2 | 5/2001 | |
| SU | 401367 | 10/1973 | |
| WO | WO92/06642 | 4/1992 | |
| WO | WO94/08524 A | 4/1994 | |
| WO | WO95/02369 | 1/1995 | |
| WO | WO95/07662 | 3/1995 | |
| WO | WO96/110453 | 7/1996 | |
| WO | WO96/13218 | 9/1996 | |
| WO | WO97/00646 | 1/1997 | |
| WO | WO97/00647 | 1/1997 | |
| WO | WO97/24073 | 7/1997 | |
| WO | WO97/24993 | 7/1997 | |
| WO | WO98/27880 | 7/1998 | |
| WO | WO99/03407 | 1/1999 | |
| WO | WO99/03408 | 1/1999 | |
| WO | WO99/03409 | 1/1999 | |
| WO | WO99/12488 | 3/1999 | |
| WO | WO99/40857 | 8/1999 | |
| WO | WO99/40861 | 8/1999 | |
| WO | WO99/51158 | 10/1999 | |
| WO | WO99/66850 | 12/1999 | |
| WO | WO99/66850 A | 12/1999 | |
| WO | WO 00/24330 | 5/2000 | |
| WO | WO 00/41638 | 7/2000 | |
| WO | WO 00/53112 | 9/2000 | |
| WO | WO 01/17448 A | 3/2001 | |
| WO | WO 01/54604 | 8/2001 | |
| WO | WO 02/07627 | 1/2002 | |
| WO | WO 02/080783 | 10/2002 | |
| WO | WO 02/080784 | 10/2002 | |
| WO | WO 02/080785 | 10/2002 | |
| WO | WO 02/080786 | 10/2002 | |
| WO | WO 02/080793 | 10/2002 | |
| WO | WO 02/080794 | 10/2002 | |
| WO | WO 02/080795 | 10/2002 | |
| WO | WO 02/080796 | 10/2002 | |
| WO | WO 02/080797 | 10/2002 | |
| WO | WO 02/080798 | 10/2002 | |
| WO | WO 02/080799 | 10/2002 | |
| WO | WO 02/081170 | 10/2002 | |
| WO | WO 03/101311 | 12/2003 | |
| WO | WO 2004/032777 | 4/2004 | |
| WO | WO 2004/052221 | 6/2004 | |
| WO | WO 2004/073490 | 9/2004 | |
| WO | WO 2004/082495 | 9/2004 | |
| WO | WO 2004/098383 | 11/2004 | |
| WO | WO 2004/103156 | 12/2004 | |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al. "Compartson of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectomy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress 1999.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.

"Reducing Needlestick Injuries in the Operating Room" Sales/Product Literature 2001.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transaction During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature 1999.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.

Muller et al., "Extended Left Hemicolectomy Using the LigaSure Vessel Sealing System" Innovations That Work,Sep. 1999.

Herman et al., "Laparoscopic Intestinal Resection With the LigaSure Vessel Sealing System: A Case Report" Innovations That Work,Feb. 2002.

Carus et al., "Initial Experience With The LigaSure Vessel Sealing System in Abdominal Surgery" Innovations That Work,Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing For Hemostasis During Gynecologic Surgery" Sales/Product Literature 1999.

Sengupta et al., "Use of a Computer-Controlled Bipolar Diathermy System in Radical Prostatectomies and Other Open Urologic Surgery" ANZ Journal of Surgery (2001) 71.9 pp. 538-540.

Olsson et al. "Radical Cystectomy in Females" Current Surgical Techniques in Urology, vol. 14, Issue 3, 2001.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

E. David Crawford "Evaluation of a New Vessel Sealing Device in Urologic Cancer Surgery" Sales/Product Literature 2000.

Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.

Dulemba et al. "Use of a Bipolar Electrothermal Vessel Sealer in Laparoscopically Assisted Vaginal Hysterectomy" Sales/Product Literature; Jan. 2004.

Johnson et al. "Evaluation of a Bipolar electrothermal Vessel Sealing Device in Hemorrhoidectomy" Sales/Product Literature; Jan. 2004.

Int'l Search Report PCT/US98/18640.
Int'l Search Report PCT/US98/23950.
Int'l Search Report PCT/US99/24869.
Int'l Search Report PCT/US01/11218.
Int'l Search Report PCT/US01/11340.
Int'l Search Report PCT/US01/11420.
Int'l Search Report PCT/US02/01890.
Int'l Search Report PCT/US02/11100.
Int'l Search Report PCT/US04/03436.
Int'l Search Report PCT/US04/13273.
Int'l Search Report PCT/US04/15311.
Int'l Search Report EP 98944778.
Int'l Search Report EP 98958575.
Int'l Search Report EP 04027314.
Int'l Search Report EP 04027479.
Int'l Search Report EP 04027705.
Int'l Search Report EP 04013772.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.

* cited by examiner

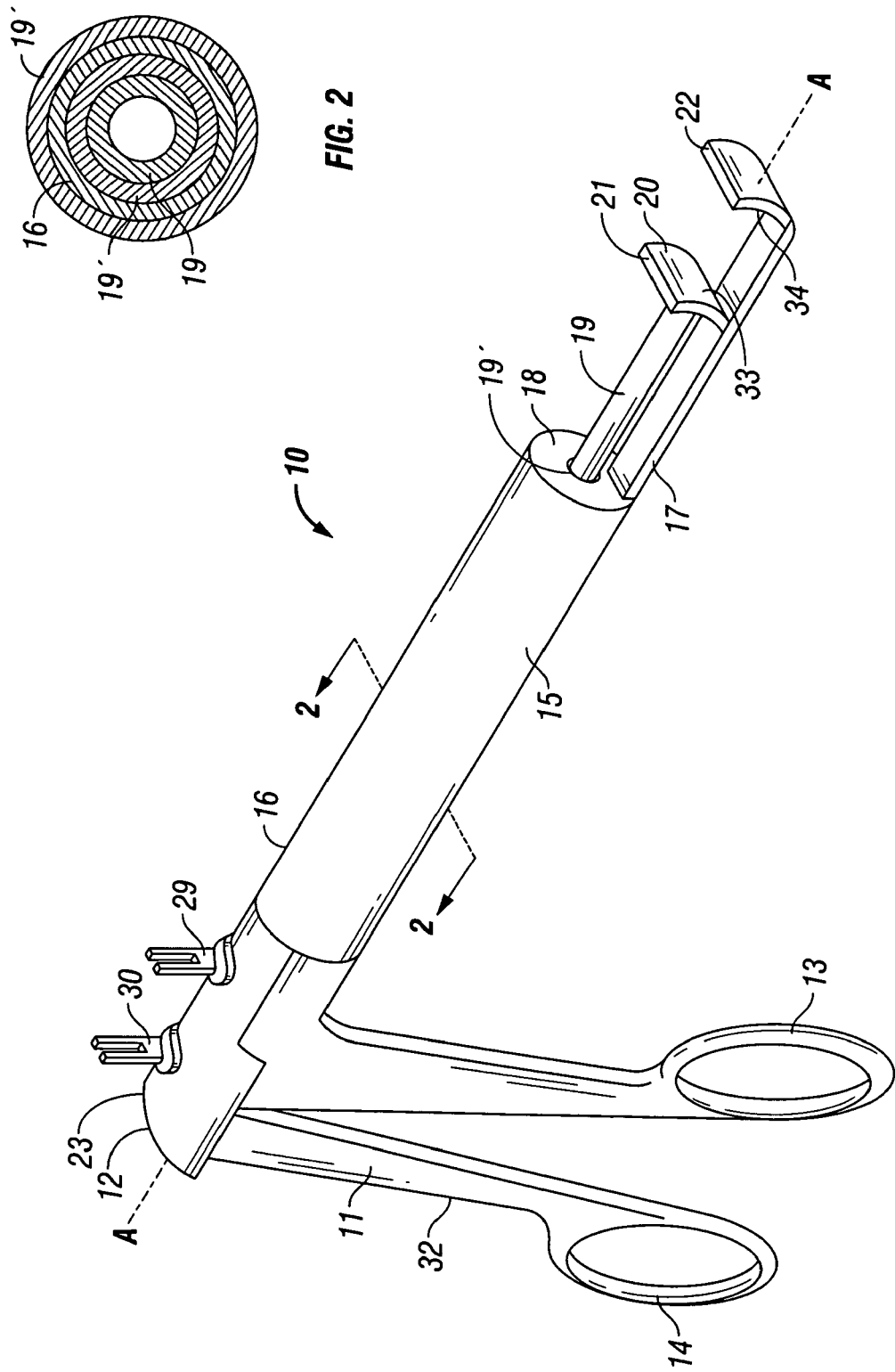

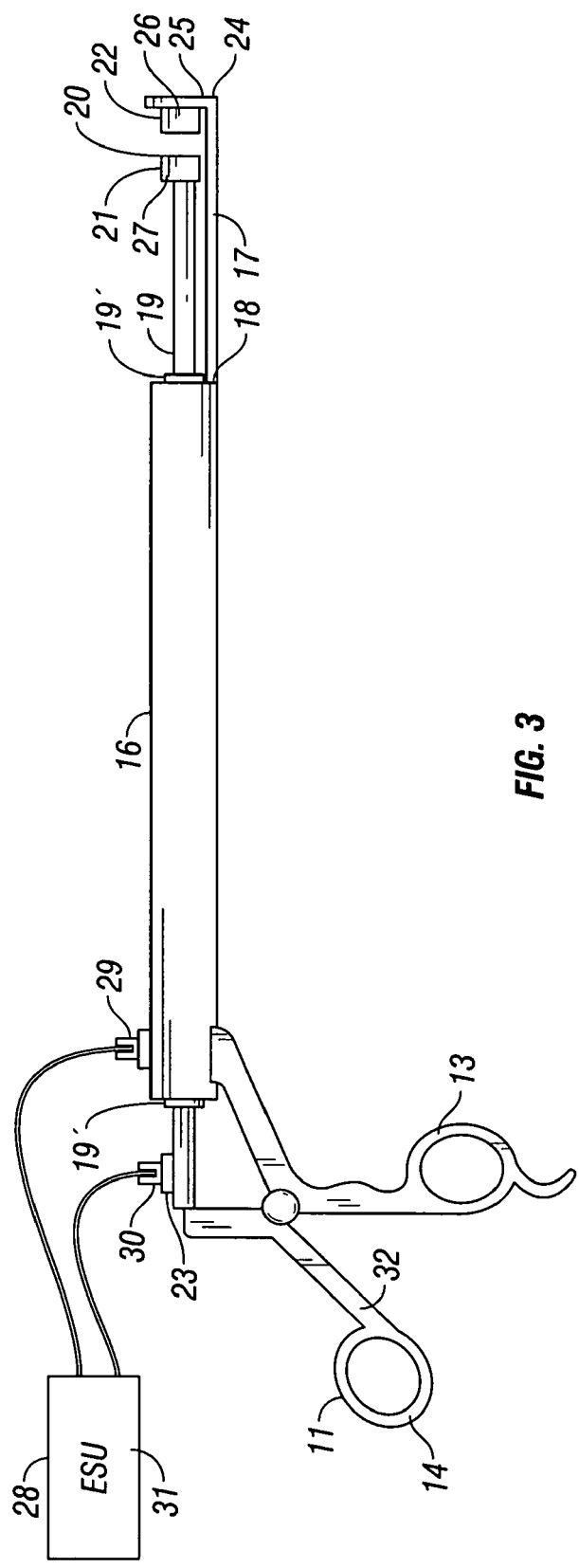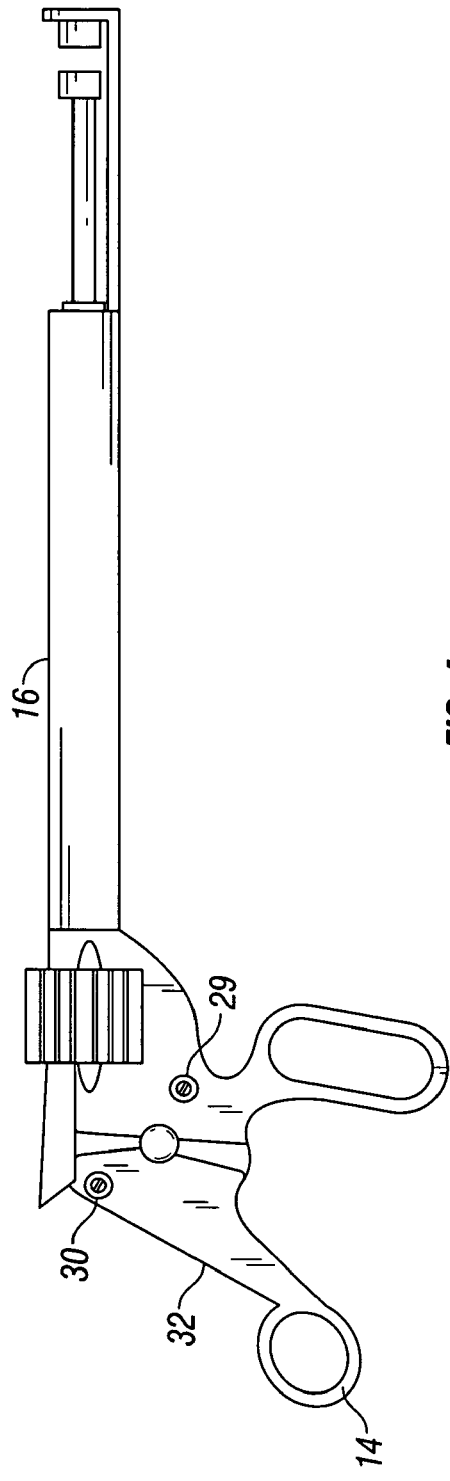

APPARATUS AND METHOD FOR SEALING AND CUTTING TISSUE

CROSS-REFERENCE TO RELATED APPLICATIONS

This application is a continuation of application Ser. No. 09/992,301, filed on Nov. 14, 2001, now U.S. Pat. No. 6,932,810 which is a continuation of U.S. application Ser. No. 09/591,328 filed on Jun. 9, 2000 now abandoned which is a continuation of U.S. application Ser. No. 08/925,805 filed Sep. 9, 1997, now U.S. Pat. No. 6,267,761.

FIELD OF THE INVENTION

This relates to an apparatus and method for cutting and sealing blood vessels or tissue using a bipolar linear travel device that compresses the tissue or vessel and then RF power is applied to seal the tissue and cut the tissue.

BACKGROUND OF THE DISCLOSURE

In order to seal blood vessels during surgery, for the purpose of defunctionalizing the vessels or to halt or prevent bleeding, radiofrequency (RF) energy can be applied to the vessel structure instead of staples or clips. Traditionally, forceps are used to create a single seal per application with bipolar RF energy. Normally, forceps that have a hinge between the tines that press against either side of the vessel are camped about tissue and power is applied. Problems are sometimes encountered with this technique because of the forceps bending or the lack of parallelism between the tines thus affecting how the tissue or vessel is compressed and sealed.

U.S. Pat. No. 5,585,896 has a percutaneous device for sealing openings in blood vessels. A balloon is inserted into the vessel and then inflated to force the vessel wall into a fixation collar.

U.S. Pat. No. 5,383,897 has a device for sealing punctures in blood vessels by conforming to the inner lumen of the vessel and placing barbs in the vessel for the purpose of sealing.

U.S. Pat. No. 5,391,183 has a device for sealing punctures in vessels by inserting hemostatic material into the puncture site and around the outside of the vessel, for the purpose of closing the puncture site.

U.S. Pat. No. 5,437,292 has a percutaneous device to seal arterial or venous puncture sites, whether accidental or intentional, which mixes fibrinogen and thrombin to form a gel around the puncture site to provide occlusion.

U.S. Pat. No. 5,411,520 has a device for percutaneously sealing blood vessels that slides down a holding catheter and enters the blood vessel with an anchor and collagen plug.

U.S. Pat. No. 5,415,657 has a device that approaches the puncture in the blood vessel, engages the outer surface and applies energy to provide hemostasis.

U.S. Pat. No. 5,429,616 has a device for sealing punctures in vessels by applying a fluid and then compressing the edges while it seals.

U.S. Pat. No. 5,441,517 has a system for sealing punctures in blood vessels by mechanically inserting a plug with an anchor to seal the puncture.

U.S. Pat. No. 5,425,739 discloses a stent placed inside the vessel to seal it or placed in such a way as to anastomose the vessel edges.

U.S. Pat. No. 5,354,271 discloses a sliding sheath for closing puncture sites that has two parts that expand radially outward and may use an accordion shape if a catheter.

U.S. Pat. No. 5,342,393 is a device that repairs punctures in vessels by clamping the tissue from both inside and outside of the vessel. Riveting is used to close the clamped sections and heat may be applied to separate the rivet from the delivery system. This device does apply heat en but only to separate the rivet from the closure site.

U.S. Pat. No. 5,176,695 is a monopolar laparoscopic mechanical cutting device with a linear reciprocating blade that sharply cuts tissue residing in its slot. The present bipolar invention does not contain a sharp blade since it seals and cuts using RF energy.

U.S. Pat. No. 3,862,630 is a device wherein ultrasonic energy is used to close off blood vessels by mechanical vibration and frictional rubbing. Any heating of the tissue is a minimal and superficial byproduct of the mechanical vibration used to seal vessels.

U.S. Pat. No. 2,011,169 is a surgical electrode with end jaws that are U-shaped and nest one inside the other. They are not insulated from each other and thus are monopolar. In the present invention the jaws are insulated and bipolar. The jaws of '169 are mounted on an endoscope. They do not fit together as in the present invention and are designed more for the purpose of removing bites out of tissue and coagulating at the same time.

All of the above devices are different from the disclosure herein for several reasons. These devices are made for wound puncture closure. This implies that a viable flow channel will remain within the lumen of the blood vessel after each device is applied. The device now disclosed remains external to the blood vessel where no puncture site would normally exist either before or after the procedure. The present device and method seals the blood vessel, and thus does not provide a pathway for blood as do the prior devices discussed. In most cases, after the sealing with the instant device and method, the vessel will still be intact, although with a seal across it. In addition, the mere clamping by the disclosed device does not seal the blood vessel. It is the application of RF energy that forms an autologous clamp causing a fusion of the intima to provide the seal.

Therefore to solve the difficulties of the prior devices a patient contacting instrument for holding and applying electrosurgical energy is shown and described. During surgical dissection, blood vessels are frequently encountered that need to be sealed and thus defunctionalized. To do this in a safe, reliable manner so the vessel is properly sealed and will not leak, a tool that applies energy to create an autologous clip is valuable and required. The device and method are briefly described. A long tube connects to one side of a bipolar power supply. The tube moves longitudinally, that is along its long axis to meet against and compress the vessel with an endpiece. The two pieces that meet on either side of the vessel could be flat, curved, triangular, angled, notched, or other shapes, as long as one fits the other. If the endpieces are of some shape other than flat, this increases the surface area that traverses the vessel creating a longer seal in the vessel without increasing the diameter of the end pieces. An applied pulse of RF power cuts the tissue after sealing. The device and method when tested on fresh vessels produced a burst pressure adequate to prove a solid seal.

Advantages of the current device and method are the parallel axial closure of the end pieces to provide a compact bipolar sealer and prevent shorting. An in-line force transducer could provide feedback information on the applied force used during surgery. The device is bipolar to assure added safety by confinement of RF current flow through the tissue between the bipolar electrodes at the end of the device.

SUMMARY OF THE INVENTION

An axially elongate bipolar tissue sealer or cutter for application of electrosurgical energy by a surgeon to the tissue and bodily fluids of a patient preferably has a handle for holding and manipulation by the surgeon. A chassis carried on the handle may extend axially relative to the handle and away from the surgeon. The chassis may be moveable to and from the handle along the axis. The chassis may have a handle end and a distal end. A tube could be carried for axial movement relative to or along the chassis. The tube is elongate relative to the chassis and has a surgeon end and a patient end disposed along its axis in the preferred embodiment.

An effector on the patient end most preferably is in position to first contact tissue upon movement axially away from the handle by the surgeon. The effector is preferably of a material for conducting electrosurgical energy. A member may be supported by the distal end of the chassis in position opposite the patient end of the tube. A pant on the member at the distal end thereof is most preferably transversely located relative to the tube axis. The part may be made of a material for conducting electrosurgical energy and to act as an opposed end effector.

A first bipolar electrosurgical electrode can be electrically connected to the effector of the patient end. A second bipolar electrosurgical electrode could be electrically connected to the part or opposed end effector. The second bipolar electrosurgical electrode is electrically isolated from the first bipolar electrosurgical electrode. An electrosurgical generator may be electrically coupled to the first and second electrosurgical electrodes. The electrosurgical generator can be arranged for selectively supplying bipolar electrosurgical energy across the first and second bipolar electrosurgical electrodes.

A mechanical activator is most preferably movably supported on the handle for use by the surgeon. The activator most preferably connects to the tube for axially moving the patient end and its end effector thereof toward or away from the part or opposed end effector. The tissue and bodily fluid between the end effectors may be sealed or cut by application of axial compression and bipolar electrosurgical energy between the first and second electrosurgical electrodes.

The end effector and the part or opposed end effector preferably include partial mating complimentary sealing or cutting surfaces for partial mating engagement upon axial movement along the axis toward one another. The end sector and/or port can be removably attached to patient end and/or member. The complimentary surfaces may be partially mated and curvelinear for providing more tissue contacting area than flat surfaces would. Alternatively, the partial mating complimentary surfaces might be parallel but skewed to the axis to provide elongate contact with axial movement between the end effector and the port. The partial mating complimentary surfaces could be substantially flat. The partial mating complimentary surfaces may be circular. The partial mating complimentary surfaces night be elliptical. The partial mating complimentary surfaces could also be triangular. The partial mating complimentary surfaces may include at least one conjugating rib and slot. The partial mating complimentary surfaces could include one or more ribs and mating slots.

A method of using an elongate along an axis tissue sealer or cutter for application by a surgeon of bipolar electrosurgical energy to tissue and bodily fluids of a patient may seal or cut. The method may have the steps of holding and manipulating by a surgeon of a handle. Extending axially a chassis and/or a tube carried on the handle might be a step. The method can have the step of moving along the axis the chassis and/or the tube with the handle. Carrying the tube for axial movement relative to and along the chassis might be a step of the method. The method step may include positioning an effector on a patient end of the tube for first contact with tissue upon movement axially away from the handle by the surgeon. Using a supported member on a distal end of the chassis in position away from the patient end of the tube can be a step of the method. The method may have the step of having a part located transversely relative to the axis and on the member.

The method of using may be performed with a first bipolar electrosurgical electrode coupled to the end effector of the patient end and a second bipolar electrosurgical electrode coupled to the part. Electrically isolating the second bipolar electrosurgical electrode from the fast bipolar electrosurgical electrode is another preferred step of the method of using. The method preferably has the step of selectively electrically coupling an electrosurgical generator to the first and second electrosurgical electrodes to supply bipolar electrosurgical RF energy from the electrosurgical generator to the first and second bipolar electrosurgical electrodes. The method most preferably has the step of a surgeon using a mechanical activator that is movably supported on the handle. Moving axially with the activator the patient end and/or the opposed end effector so that tissue and bodily fluid therebetween may be sealed or cut between the end effector and the part through the application of compression and bipolar electrosurgical energy between the first and second electrosurgical electrodes is a preferred step.

The method may have the steps of applying the provided effector with the partially mating complimentary sealing or cutting surfaces, and partially mating engagement of the complimentary sealing or cutting surfaces upon axial movement toward one another along the axis. The method might use the step of removably attaching the part and/or end effector to the member and the chassis respectively. The method has the step of using partially mating the complimentary surfaces engagable along curvelinear paths for providing more tissue contacting area than between flat surfaces. The method has the step of using the partially mating the complimentary surfaces preferably parallel but along a plane skewed to the axis to provide elongate contact with anal movement between the end effector and the port.

The method may have the step of using the partially mating complimentary flat surfaces that are perhaps along the planes of the flat surfaces. The method could have the step of using partially mating complimentary circular surfaces that might be along the arcs of the circular surfaces. The method might have the step of using partially mating complimentary elliptical surfaces which are preferably along the curves of ellipses. The method can have the step of using partially mating complimentary triangular surfaces along edges of the triangles. The method could have the step of using partially mating complimentary surfaces by engaging at least one conjugating rib with a slot. The method may have the step of using partially mating complimentary surfaces that may include one or more ribs and companion slots.

BRIEF DESCRIPTION OF THE DRAWINGS

FIG. 1 is a perspective view of an elongated tubular bipolar tissue sealer or cutter for application by a surgeon of electrosurgical energy to the tissue, the sealer or cutter slides along its axis with an internal, concentric sliding portion for axially bring together the end effectors.

FIG. 2 is a view in cross section as would be seen along lines 2-2 in FIG. 1.

FIG. 3 is a side view of a reusable elongate tubular bipolar tissue sealer or cutter as in FIG. 1 with one of the various end effectors having partially mating complimentary FIG. 4 is a side view of a disposable elongate tubular bipolar tissue sealer or cutter as in FIG. 1 with one of the various end effector having partially mating

DETAILED DESCRIPTION OF THE INVENTION

Figure 5:
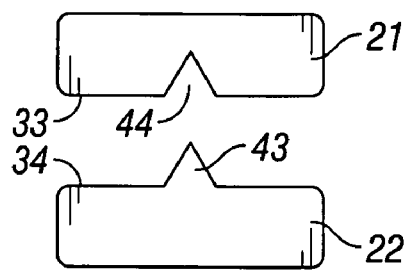
FIG. 5 is an enlarged top view of the part and of the end effector with partially mating complimentary surfaces that nest with V shaped conjugating jaws.

FIG. 1 is a perspective view of an elongate tubular bipolar tissue sealer or cutter 10 for application by a surgeon of electrosurgical energy to tissue. A handle 11, for holding and manipulation by the surgeon, is on a proximal end 12 of the elongate bipolar tissue sealer or cutter 10. The handle 11 has both first and second handle grips 13 and 14, respectively. A chassis 15, carded on the handle 11 by mechanical connection with the first handle grip 13, extends axially along axis "A" relative to the handle 11 and away from the surgeon a distance adequate to reach the patient's operative site. The chassis 15 is comprised of at least two parts. The first is an outer tube 16 which extends from the handle 11 along the axis "A." The outer tube 16 is fixed on the chassis 15. The second part is a member or chassis extension 17 extending from a patient end 18 of the outer tube 16, also along the axis "A." An inner tube 19 is moveable to and from the handle 11 in the preferred embodiment. The inner tube 19 is guided along the axis "A." The inner tube 19 connects to the second handle grip 14 for surgeon access. A distal end 20 is on the inner tube 19 and faces the operative site. The elongate tubular sealer or cutter 10 thus in part slides along its axis "A" with inner tube 19 which is an internal, concentric slider to axially bring together end effectors 21 and 22. Inner tube 19 is telescopically carried, in the preferred embodiment, on the chassis 15 for axial movement relative to and therealong. The inner tube 19 has relative to the chassis 15, a surgeon end 23 and the distal end 20 which are disposed along the axis "A" thereof as shown in FIGS. 1 and 3. FIG. 2 is a view of the inner and outer tubes 19 and 16 in cross section as would be seen along lines 2-2 in FIG. 1. The preferred outer and inner tubes 16 and 19 are metallic and thus should be insulated from each other and from the user by a coating 19' as seen in FIG. 2.

End effector 21 on the distal end 20 is in position to contact tissue upon movement axially away from the handle 11 by the surgeon's manipulation of second handle grip 14. FIG. 3 is a side view of the reusable elongate tubular structure of FIG. 1 with both of the various end effectors 21 and 22 shown from the side. The effector 21 and 22 are made of materials for conducting electrosurgical energy such as metal, conductive polymer or ceramic. The end effector 22 has member 24 supported by the chassis extension 17 normal thereto in position opposite the patient end 20 of the inner tube 19. A part 25 on the member 24 thereof is transversely located relative to the axis "A" in FIG. 1. The end effectors 21 and 22 are thus opposed for engagement upon relative axial displacement of the inner tube 19 and/or chassis 15. FIG. 4 is a side view of a disposable elongate tubular structure of FIG. 1 with one of the various end effectors 21 and 22 shown from the side in FIG. 3. As shown in FIG. 3 the chassis extension 17, member 24, and part 25 are made for conducting electrosurgical energy. Of course, lion can be added as needed to direct the bipolar electrosurgery to the space between the end effectors 21 and 22.

A first bipolar electrosurgical electrode 26 for contact with the patient's tissue or bodily fluids is electrically coupled to the effector 22 beyond the patient end 18. A second bipolar electrosurgical electrode 27 is electrically coupled to the effectors 21 and 22 for contact with the patient's tissue or bodily fluids. The second bipolar electrosurgical electrode 27 is electrically isolated from the first bipolar electrosurgical electrode 26 but is in position to deliver bipolar electrosurgical energy across tissue held therebetween. An electrosurgical generator 28, in FIG. 3, is electrically coupled to the first and second electrosurgical electrodes 26 and 27 through terminals 29 and 30, respectively. The electrosurgical generator 28 can be arranged for selectively supplying bipolar electrosurgical energy to the first and second bipolar electrosurgical electrodes 26 and 27. Selective application of electrosurgical energy is in response to the surgeons control and/or a sensor 31 in the electrosurgical generator 28. Sensor 31 may measure impedance across the tissue between the electrodes 26 and 27.

A mechanical activator 32, in FIG. 3, is preferably movably supported on the handle 11 for use by the surgeon. The mechanical activator 32 connects to the inner tube 19 for axially moving the end effector 21 thereof toward or away from the end effector 22 in the preferred embodiment. The tissue and bodily fluid therebetween may be sealed or cut between the end effectors 21 and 22 through the combined application of compression and bipolar electrosurgical energy between the first and second electrosurgical electrodes 26 and 27.

Figure 8:
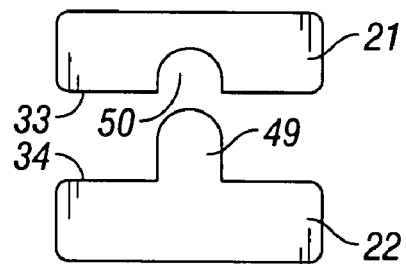
FIG. 8 is an enlarged top view of the part and the end effector with partially mating complimentary surfaces that nest with a pedistaled male and a flush female wherein both are U shaped conjugating jaws.
Figure 9:
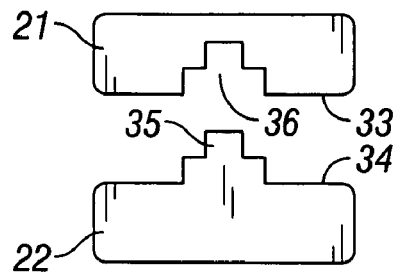
FIG. 9 is an enlarged top view of the part and end effector with partially mating complimentary surfaces that nest with a terraced male and a recessed female shaped to fit as conjugating jaws.
Figure 10:
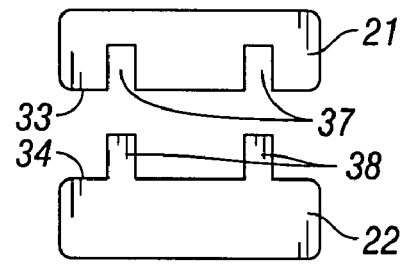
FIG. 10 is an enlarged top view of the part and the end effector with partially mating complimentary surfaces that nest with a pair of upstanding ribs and a conjugating pair of kerfs as the jaws.
Figure 11:
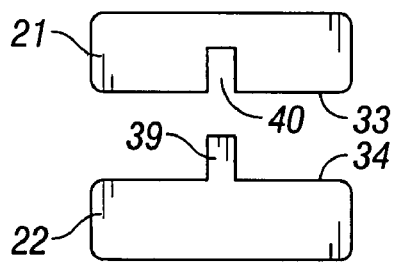
FIG. 11 is an enlarged top view of the part and the end effector with partially mating complimentary surfaces that nest with a single upstanding rib and conjugating kerf as the jaws.
Figure 12:
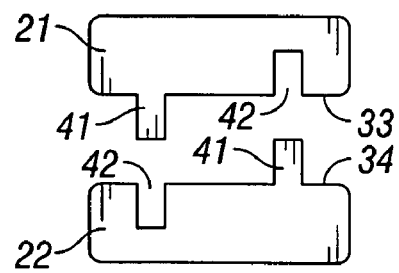
FIG. 12 is an enlarged top view of the part and the end effector with part mating complimentary surfaces that nest with a pair of upstanding ribs and conjugating kerfs wherein therein one rib and one kerf is on the end effector across from its companion kerf and rib on the part as the jaws.
Figure 13:
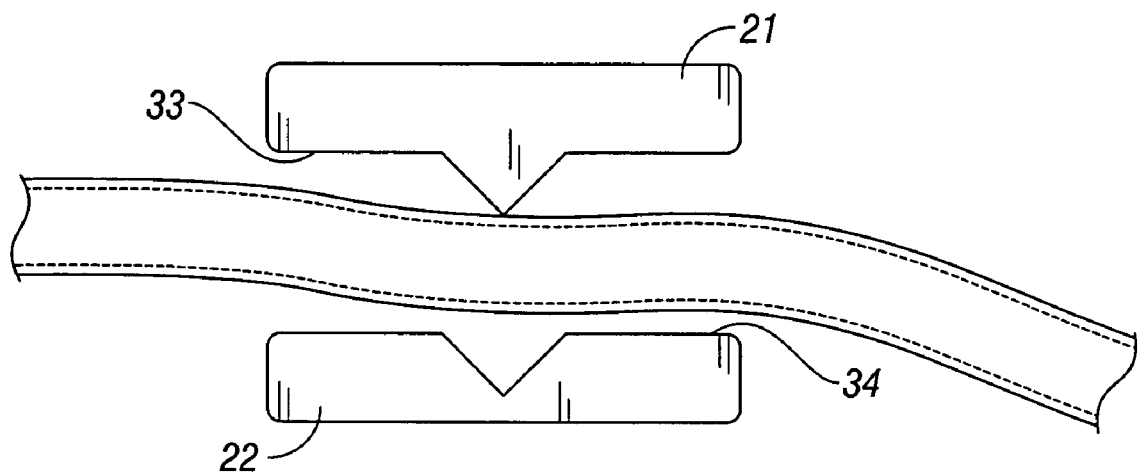
FIG. 13 illustrates the conjugating jaws of FIG. 5 with a vessel therebetween prior to sealing.
Figure 14:
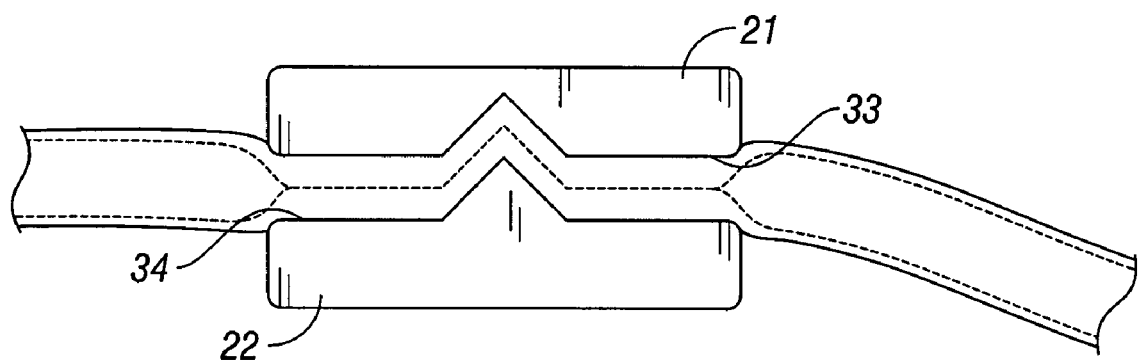
FIG. 14 illustrates the conjugated jaws of FIG. 5 with a vessel therebetween during sealing.
Figure 15:
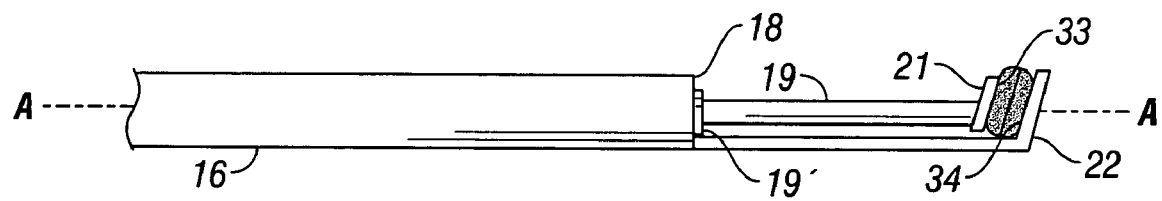
FIG. 15 is a partial enlarged view of the end effector and the part of FIG. 1 viewed from above with an open vessel clamped therebetween during the process of sealing.

The end effectors 21 and 22 include complimentary sealing or cutting surfaces 33 and 34 for partial mating engagement upon their axial movement toward one another along the axis "A." FIG. 13 illustrates end effectors 21 and 22 or the conjugating jaws of FIG. 5 with a vessel therebetween prior to sealing. Similarly, FIG. 14 illustrates end effectors 21 and 22 or the conjugating jaws of FIG. 5 with a vessel therebetween during sealing. The end effectors 21 and 22 could be removably attached to the member 24 and/or the inner tube 19, respectively. FIG. 15 is a partial enlarged view of the end effectors 21 and 22 of FIG. 1 viewed from the side with an open vessel clamped therebetween during the method or process of sealing. The partial mating complimentary surfaces 33 and 34 in FIG. 8 are curvelinear for providing more tissue contacting area than flat surfaces of the same width would. In FIG. 8 the end effectors 21 and 22 have conjugating complimentary surface 33 and 34 that nest configured with a pedistaled male part 49 and a mating U shaped female part 50 for the jaws. FIG. 9 is an enlarged top view of end effectors 21 and 22 showing conjugating surfaces that nest with a male part 35 terraced and a female part 36 shaped to fit as jaws FIG. 10 is an enlarged top view of end effectors 21 and 22 showing conjugating surfaces that nest with a pair of upstanding ribs 38 and a complimentary pair of kerfs 37 as the jaws. FIG. 11 is an enlarged top view of the end effectors 21 and 22 showing conjugating surfaces that nest with a single upstanding rib 39 and a complimentary kerf 40 as the jaws. FIG. 12 is an enlarged top view of end effectors 21 and 22 showing conjugating surfaces that nest with a pair of upstanding opposite ribs 41 and complimentary opposed kerfs 42 wherein therein one rib 41 is on each of the end effectors 21 and 22 across from its complimentary kerf 42 on the opposite end effectors either 21 or 22.

Figure 6:
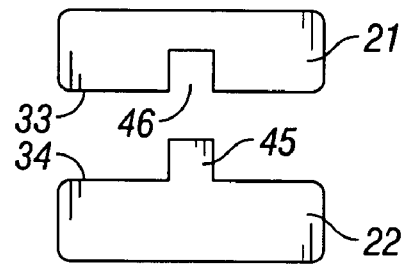
FIG. 6 is an enlarged top view of the part and the end sector with partially mating complimentary surfaces that nest with rib and slot conjugating jaws.
Figure 7:
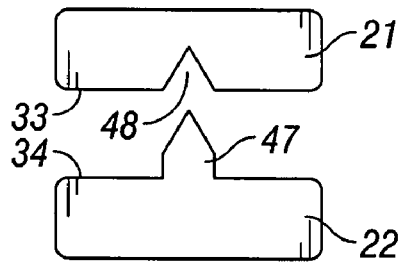
FIG. 7 is an enlarged top view of the part and the end effector with partially mating complimentary surfaces that nest with a pedistaled male and a flush female wherein both are V shaped conjugating jaws.

Any complimentary mating curvelinear jaws even "S" shaped or those shown in FIG. 1 could be arranged to provide more surface area for contact than the flat surfaces defined by the cords thereacross. FIG. 5 is an enlarged top view end effectors 21 and 22 showing conjugating surfaces 33 and 34 that nest with V shaped complimentary jaws 43 and 44. FIG. 6 is an enlarged top view of end effectors 21 and 22 showing conjugating surfaces 33 and 34 that nest with a rib 45 and a channel 46 as complimentary jaws FIG. 7 is an enlarged top view of end effectors 22 and 23 showing conjugating surfaces 33 and 34 that nest with a male part pedistaled 47 and V shaped female part 48 as complimentary jaws.

The partial mating complimentary surfaces 33 and 34 might be parallel but skewed to axis "A" as in FIG. 15 to provide elongate contact with axial movement between the inner tube 19 and chassis 15 thus keeping the size of the laparoscopic portal through which the end effectors 21 and 22 must pass to a minimum transverse dimension. The partial mating complimentary surfaces 33 and 34 could be substantially fat as in FIGS. 3 and 4. The partial mating complimentary surfaces 33 and 34 may be circular sections such as appear in FIGS. 1 and 8. The partial mating complimentary surfaces 33 and 34 might be elliptical and thus similar to FIGS. 1 and 8 with the curvatures being a part of an ellipse instead of a circle. Because of the perspective showing in FIG. 1, the observable differences in such an illustration between a circle and an ellipse can not be perceived. The partial mating complimentary surfaces 33 and 34 could also be triangular as in FIGS. 5, 7, 13 and 14. The partial mating complimentary surfaces 33 and 34 may include at least one conjugating rib and slot as in FIGS. 6 and 11. The partial mating complimentary surfaces 33 and 34 could include several ribs as in FIGS. 10 and 12.

A method of applying the elongate tubular bipolar tissue sealer or cutter 10 along an axis "A" includes use by a surgeon to deliver bipolar electrosurgical energy to the tissue and bodily fluids of a patient. The method has the steps of holding and manipulating the handle 11 by the surgeon. Extending axially inner tube 19 and/or the chassis 15 carried on the handle 11 away from the surgeon is a step. The method can have the step moving the inner tube 19 relative to the chassis 15 along the axis "A."Carrying inner tube 19 for axial movement relative to and along the chassis 15 is a step of the preferred method. The method step includes positioning end effector 22 on the patient end 18 to fire contact tissue upon movement axially of the inner tube 19 by the surgeon. Using a supported member 24 the chassis 15 is a step of the method. The method may have the step of using a part 25 located transversely relative to the axis "A" and on the member 24.

The method of using has a first bipolar electrosurgical electrode 26 coupled to the end effector 22 extending from the patient end 18 and a second bipolar electrosurgical electrode 27 coupled to the end effector 21. Electrically isolating the second bipolar electrosurgical electrode 27 from the first bipolar electrosurgical electrode 26 is another preferred method step for using. The method preferably has the step of selectively coupling electrically an electrosurgical generator 28 to the first and second electrosurgical electrodes to supply bipolar electrosurgical energy from the electrosurgical generator to the first and second bipolar electrosurgical electrodes 26 and 27. The method most preferably has the step of a surgeon using a mechanical activator 32 movably supported on the handle 11. Moving anally with the mechanical activator 32 the inner tube 19 and the end effector 21 thereof toward or away from the end effector 22 so that tissue and bodily fluid therebetween may be sealed or cut between the end effectors 21 and 22 the application of compression and bipolar electrosurgical energy between the first and second electrosurgical electrodes 26 and 27 is a preferred step.

Figure 16:
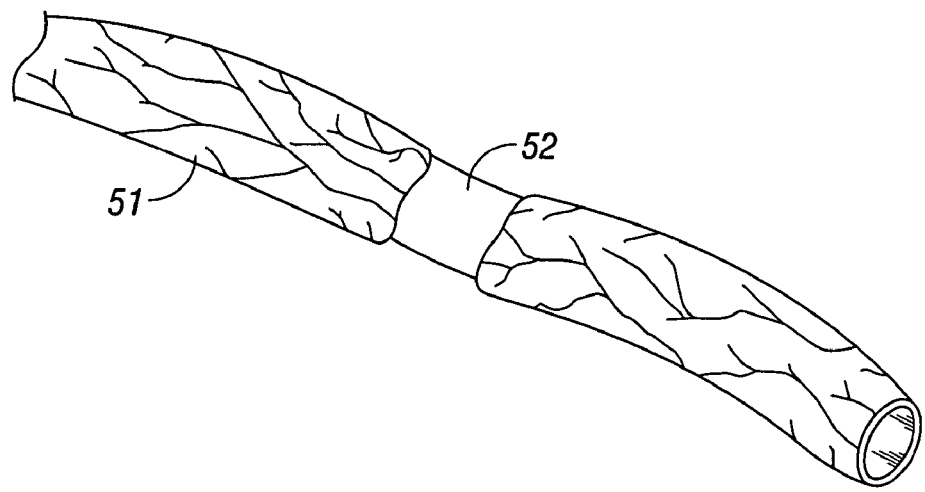
FIG. 16 is a perspective illustration of a sealed vessel.

The method may have the steps of applying the provided end effectors with partially complimentary sealing or cutting surfaces 33 and 34, and partially mating engagement of the complimentary sealing or cutting surfaces 33 and 34 upon axial movement toward one another along the axis "A." FIG. 16 is a perspective illustration of a sealed vessel 51 as a consequence of performing the method to form seal 52. The method might use the step of choosing to removably attach the end effectors 26 and 27, inner tube 19 and the chassis 15, respectively. The method has the step of using partially mating the complimentary surfaces 33 and 34 engagable along curvelinear paths for providing more tissue contacting area than between flat surfaces. The method has the step of using the partially mating the complimentary surfaces 33 and 34 preferably parallel along a plane skewed to the axis "A" to provide elongate contact with anal movement between the inner tube 19 and chassis 15.

The method has the step of using the partially mating complimentary flat surfaces 33 and 34 that are perhaps along the planes of the flat surfaces. The method has the step of using the partially mating complimentary circular surfaces 33 and 34 that might be along the arcs of the circular surfaces. The method has the step of using the partially mating complimentary elliptical surfaces 33 and 34 which are preferably along the curves of the ellipses. The method has the step of using the partially mating complimentary triangular surfaces 33 and 34 that can be along edges of the triangles. The method has the step of using the party mating complimentary surfaces 33 and 34 by engaging at least one conjugating and slot. The method has the step of using the partially mating complimentary faces 33 and 34 that include one or more ribs.

The preferred elongate tubular bipolar tissue sealer or cutter 10 for application of electrosurgical energy to tissue by a surgeon as covered in the claims that follow has structure that slides along its axis "A" with an internal, concentric sliding portion. The inner or inside sliding tube 19 is attached to the proximal end effector 21 and the external fixed tube or chassis 15 connects to the distal end effector 22 in the preferred embodiment. The two end effectors 21 and 22 are matched so that the distal end effector 22 fits snugly against the proximal end effector 21. These end effectors 21 and 22 can be any of a number of conjugating shaped pairs including triangular, spherical, rectangular, with or without a notch. The notch is not just for alignment but also may define a sharp edge to sever the tissue or vessel by application of a pulse of high-power RF to the clamped site of tissue in between the end effectors 21 and 22. In the preferred embodiment, the handle 11 is squeezed so the inner tube 19 slides away the user and the chassis 15 is fix in relation to the inner tube 19 as the end sectors 21 and 22 act on the tissue therebetween. Of course it can be reversed so the chassis 15 moves and the inner tube 19 is fixed.

What is claimed is:

1. A bipolar electrosurgical system for sealing and cutting tissue, comprising:
    an electrosurgical generator;
    a tissue sealing instrument including a chassis having a longitudinal axis defined therethrough and first and second end effectors attached thereto, one of said first and second end effectors being movable along said longitudinal axis relative to the other of said first and second end effectors from a first position for positioning tissue therebetween to a second position for grasping tissue between said first and second end effectors, wherein said first and second end effectors include complimenting vessel sealing electrodes which partially matingly engage one another, said electrodes adapted to be connected to the electrosurgical generator such that the electrodes are capable of sealing and cutting tissue disposed therebetween upon activation of said electrodes;
    an activator for moving said end effectors from the first to second positions;
    a sensor disposed within the electrosurgical generator which measures the impedance across the tissue held between said end effectors;
    means for selectively applying electrosurgical energy from the electrosurgical generator to said end effectors in response to the impedance measurement across the tissue from said sensor; and
    wherein the chassis is operatively connected to at least one tube.

2. A bipolar instrument according to claim 1 wherein the activator includes a handle, the handle including at least one handle grip.

3. A bipolar instrument according to claim 1 wherein the chassis includes an inner tube and an outer tube.

4. A bipolar instrument according to claim 1 wherein the first and second end effectors include complimentary vessel contacting surfaces which partially matingly engage upon movement of the end effectors from the first to second positions.

5. A bipolar instrument according to claim 4 wherein the complimentary vessel contacting surfaces are curvilinear.

6. A bipolar instrument according to claim 4 wherein the complimentary vessel contacting surfaces are substantially flat.

7. A bipolar instrument according to claim 4 wherein the complimentary vessel contacting surfaces are triangular.

8. A bipolar instrument according to claim 4 wherein the complimentary vessel contacting surfaces further include nibs.

* * * * *